United States Patent
Dumesic et al.

(10) Patent No.: US 8,404,890 B2
(45) Date of Patent: Mar. 26, 2013

(54) PRODUCTION OF 2,4-HEXADIENOIC ACID AND 1,3-PENTADIENE FROM 6-METHYL-5,6-DIHYDRO-2-PYRONE

(75) Inventors: James A. Dumesic, Madison, WI (US); Mei Chia, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 161 days.

(21) Appl. No.: 12/943,433

(22) Filed: Nov. 10, 2010

(65) Prior Publication Data

US 2012/0116119 A1 May 10, 2012

(51) Int. Cl.
- *C07C 57/10* (2006.01)
- *C07C 45/60* (2006.01)
- *C07C 5/48* (2006.01)

(52) U.S. Cl. .......... 562/601; 568/386; 585/327

(58) Field of Classification Search .......... None
See application file for complete search history.

(56) References Cited

U.S. PATENT DOCUMENTS 6,525,218 B2  2/2003  Kouno et al.

FOREIGN PATENT DOCUMENTS

JP  54-163516  12/1979

OTHER PUBLICATIONS

Takagaki et al, Chemistry Letters, Glucose to Value-added Chemicals: Anhydroglucose Formation by Selective Dehydration over Solid Acid Catalysts, 2009, 38(7), pp. 650-651.*

Barcardit et al., "Hydrogenations of Triacetic Acid Lactone, A New Synthesis of The Carperter Bee (*Xylocopa hirsutissima*) Sex Pheromone," *Tetrahedron Lett.*, 21:551-554 (1980).
Casas et al., "Pentadiene production from potassium sorbate by osmotolerant yeasts," *International Journal of Food Microbiology*, 94(1):93-96 (2004).
Fownes, G., "A Manual of Elementary Chemistry, 11$^{th}$ Ed.," Henry C. Lea, Philadelphia, PA, p. 632 , 1872.
Richardson et al., "Tolerance and Specificity of Recombinant 6-Methylsalicyclic Acid Synthase," *Metabolic Eng.* 1:180-187 (1999).
Xie et al., Microbial Synthesis of Triacetic Acid Lactone, *Biotech. Bioeng.*, vol. 93, No. 4, pp. 727-736 (2006).
Zha et al., "Rational Pathway Engineering of Type I Fatty Acid Synthase Allows the Biosynthesis of Triacetic Acid Lactone from D-Glucose in Vivo," *J. Am. Chem. Soc.*, 126:4534-4535 (2004).

* cited by examiner

*Primary Examiner* — Paul A Zucker
(74) *Attorney, Agent, or Firm* — Joseph T. Leone, Esq.; Daniel A. Blasiole; DeWitt Ross & Stevens S.C.

(57) ABSTRACT

Described is a method of making sorbic acid, pentadiene, or 3-penten-2-one. The method includes partially hydrogenating 4-hydroxy-6-methyl-2-pyrone (HMP) to yield 5,6-dihydro-4-hydroxy-6-methyl-2H-pyran-2-one (4-DHMMP). Then, if 3-penten-2-one is desired, thermally decomposing the 4-DHMMP to yield 3-penten-2-one. If sorbic acid or pentadiene are desired, the 4-DHMMP is hydrogenated to yield 4-hydroxy-6-methyltetrahydro-2-pyrone (4-HMTHP). The 4-HMTHP is then dehydrated by contacting it with a solid acid catalyst to yield parasorbic acid (PSA). The PSA can then be ring-opened by contacting it with a solid acid catalyst. The reaction conditions of the ring-opening reaction can be controlled to yield sorbic acid and/or pentadiene.

25 Claims, No Drawings

PRODUCTION OF 2,4-HEXADIENOIC ACID AND 1,3-PENTADIENE FROM 6-METHYL-5,6-DIHYDRO-2-PYRONE

FEDERAL FUNDING STATEMENT

This invention was made with Government support under 0813570 awarded by the National Science Foundation. The United States Government has certain rights in the invention.

FIELD OF THE INVENTION

The invention is directed to a method of making 2,4-hexadienoic acid (i.e., sorbic acid), 1,3-pentadiene, and related compounds via an acid-catalyzed, ring-opening of 6-methyl-5,6-dihydro-2-pyrone (i.e., parasorbic acid).

BACKGROUND

A. W von Hofmann was the first to isolate sorbic acid (2,4-hexadienoic acid) in 1859 (by distilling oil pressed from the berries of mountain ash trees.). The distillation yields the corresponding lactone, which Hofmann then converted to the acid by hydrolysis. Its antimicrobial properties were not extensively explored until after the close of World War II. Since the 1950's, sorbic acid (E200) has been used extensively worldwide as a preservative in a vast array of foods. For example, sorbic acid has been used since the late 1950's as a preservative in white wines. Sorbic acid and its salts (notably potassium sorbate, E202) are also used as inhibitors of Clostridium botulinum in processed meat products. Sorbic acid and its salts are commodity products; worldwide production of sorbates in 2008 was approximately 65,000 metric tons (i.e., tonnes; 71,650 US short tons).

The benefits of sorbates as food preservatives are two-fold: sorbates inhibit a very wide spectrum of bacteria, yeasts, and molds; and sorbates have extremely low toxicity (lower even than table salt, NaCl). Sorbates are "generally regarded as safe" (GRAS) by the U.S. Food and Drug Administration.

There are several known protocols for producing sorbic acid and sorbates. Commercial quantities are typically produced by polymerizing crotonaldehyde and ketene to form an intermediate polyester, decomposing the polyester to yield a crude sorbic acid, and then subjecting the crude sorbic acid to a variety of purification steps to yield various grades of sorbic acid (e.g., food grade). The intermediate polyester is decomposed by a number of means, including treating it with strong acid, strong base, or via heat. The required decomposition step is problematic because it yields unwanted, colored by-products. To yield the highest grades of product (i.e., food grade sorbate or better) multiple purification steps are required.

Japanese Examined Patent Application Publication No. 44-26646 discloses a process for producing sorbic acid in which the polyester obtained by the reaction between crotonaldehyde and ketene is decomposed with hydrochloric acid, followed by cooling and filtrating the resulting reaction mixture to yield crude sorbic acid. The crude sorbic acid is then dissolved in hot water to which is added activated carbon. The reaction mixture is filtered hot, and the filtrate is gradually cooled to yield crystalline sorbic acid.

A related protocol is described in Japanese Unexamined Patent Application Publication No. 54-163516. Here, the polyester obtained from reacting crotonaldehyde and ketene is decomposed with hydrochloric acid in the presence of a urea compound. The resulting decomposition reaction mixture is filtered to yield crude sorbic acid. Aqueous sodium hydroxide solution is added to the crude sorbic acid to yield an aqueous sodium sorbate solution. The aqueous sodium sorbate solution is treated with activated carbon, neutralized, and cooled to crystallize the purified sorbic acid.

See also U.S. Pat. No. 6,525,218, which describes a process in which the intermediate polyester (the reaction product between crotonaldehyde and ketene) is hydrolyzed with an aqueous hydrochloric acid solution having a concentration of from 3 to 10% by weight under a pressure greater than atmospheric pressure.

These prior art processes for making sorbates are less than ideal because of the formation of by-products (tar, etc. formed during the decomposition step), and yield losses during the solid-liquid separation steps.

1,3-Pentadiene (also known as piperylene) is a volatile, flammable, linear five-carbon hydrocarbon. It is widely used as a monomer in the production of plastics, adhesives, and resins. It is produced commercially as a by-product of ethylene production via the catalytic cracking of naphtha. There is no other means known to produce 1,3-pentadiene in commercial quantities. However, there have been efforts to genetically engineer microorganisms such as yeast to produce 1,3-pentadiene. See Casasa et al. (1 Jul. 2004) "Pentadiene production from potassium sorbate by osmotolerant yeasts," International Journal of Food Microbiology, 94(1):93-96.

SUMMARY OF THE INVENTION

As noted above, described herein is a method of making 2,4-hexadienoic acid (i.e., sorbic acid), 1,3-pentadiene (i.e., piperylene), and related compounds via an acid-catalyzed, ring-opening of 6-methyl-5,6-dihydro-2-pyrone (i.e., parasorbic acid). These products are commercially significant: sorbic acid as a food preservative; and 1,3-pentadiene as a chemical intermediate for producing resins and adhesives. The sole commercial source of 1,3-pentadiene is from the $C_5$ fraction of naphtha cracking. A primary advantage and benefit of the method described and claimed herein is that the parasorbic acid can be made from a renewable precursor, 4-hydroxy-6-methyl-2-pyrone (HMP).

A first version of the invention is directed to a method of making sorbic acid and pentadiene. Here, the method comprises converting a renewable feedstock, 4-hydroxy-6-methyl-2-pyrone (HMP) into parasorbic acid (PSA). The ring of the PSA is then opened by contacting the PSA with a solid acid catalyst. This can be done with dehydration of the opened ring to yield sorbic acid, or with decarboxylation of the opened ring to yield pentadiene. The conversion of HMP to PSA is preferably accomplished via hydrogenating the HMP in the presence of a catalyst comprising one or more noble metals, such as a catalyst comprising palladium or a mixture of palladium and niobium. The conversion of HMP to PSA preferably takes place in a solvent selected from the group consisting of $C_1$- to $C_6$-alcohols and $C_1$- to $C_6$-carboxylic acids. The conversion of HMP to PSA may take place in a single step, or in multiple steps, such as hydrogenating the HMP to yield 5,6-dihydro-4-hydroxy-6-methyl-2H-pyran-2-one (4-HMTHP), and then dehydrating the 4-HMTHP by contacting it with a solid acid catalyst to yield PSA. The ring-opening reactions are preferably carried out in a polar, aprotic solvent, or a mixed solvent comprising water and a polar, aprotic solvent.

Another version of the method is directed to making sorbic acid and pentadiene in a more specific, three-step approach:

(a) hydrogenating 4-hydroxy-6-methyl-2-pyrone (HMP) to yield 4-hydroxy-6-methyltetrahydro-2-pyrone (4-HMTHP); and then (b) dehydrating the 4-HMTHP from step (a) by contacting the 4-HMTHP with a solid acid catalyst to yield parasorbic acid (PSA); and then (c) ring-opening the PSA from step (b) by contacting the PSA with a solid acid catalyst to yield sorbic acid or pentadiene.

Yet another version of the method also enables the production of 3-penten-2-one by thermal degradation of one of the intermediates. Here, the method is directed to making any or all of sorbic acid, pentadiene, or 3-penten-2-one. The method comprises first partially hydrogenating HMP to yield 4-DHMMP. Then, if 3-penten-2-one one of the desired products, thermally decomposing all or a portion of the 4-DHMMP to yield 3-penten-2-one. If sorbic acid or pentadiene are the desired products, all or a portion of the 4-DHMMP is hydrogenated to to yield 4-hydroxy-6-methyltetrahydro-2-pyrone (4-HMTHP). The 4-HMTHP is then dehydrated by by contacting it with a solid acid catalyst to yield parasorbic acid (PSA). The ring-opening of the PSA then proceeds as described above to yield sorbic acid or pentadiene.

As noted herein, many of the reactions are catalyzed by heterogeneous (i.e., solid) acid catalysts. The solid acid catalysts for use in the present invention may comprise one or more solid acid materials without limitation, whether now known or developed in the future. The solid acid catalyst can be used independently or alternatively can be utilized in combination with one or more mineral acid or other types of catalysts. Exemplary solid acid catalysts which can be utilized include, but are not limited to, heteropoly acids, acid resin-type catalysts, meso-porous silicas, acid clays, sulfated zirconia, molecular sieve materials, zeolites, and acidic material on a thermo-stable support. Where an acidic material is provided on a thermo-stable support, the thermo-stable support can include for example, one or more of silica, tin oxide, niobia, zirconia, titania, carbon, alpha-alumina, and the like. The oxides themselves (e.g., ZrO2, SnO2, TiO2, etc.) which may optionally be doped with additional acid groups such as SO42-may also be used as solid acid catalysts.

Further examples of suitable solid acid catalysts include strongly acidic ion exchangers such as cross-linked polystyrene containing sulfonic acid groups. For example, the Amberlyst®-brand resins are functionalized styrene-divinylbenzene copolymers with different surface properties and porosities. The functional group is generally of the sulfuric acid type. The Amberlyst®-brand resins are supplied as gellular or macro-reticular spherical beads. (Amberlyst® is a registered trademark of the Dow Chemical Co.) Similarly, Nafion®-brand resins are sulfonated tetrafluoroethylene-based fluoropolymer copolymers which are solid acid catalysts. Nafion® is a registered trademark of E.I. du Pont de Nemours & Co.)

Zeolites may also be used as solid acid catalysts. Of these, H-type zeolites are generally preferred, for example zeolites in the mordenite group or fine-pored zeolites such as zeolites X, Y and L, e.g., mordenite, erionite, chabazite, or faujasite. Also suitable are ultrastable zeolites in the faujasite group which have been dealuminated.

The hydrogenation reactions described herein are preferably carried out using a noble metal-containing catalyst, that is, a catalyst comprising one or metals selected from the group consisting of Ru, Rh, Pd, Ag, Os, Ir, Pt, or Au. The noble metals may be in elemental form or in the form of oxides, sulfides, nitrates, other salts, etc. They may also be alloyed or admixed with other metals, metal oxides, metal salts, etc. The noble metal-containing catalysts may optionally be disposed on a solid support such as carbon, titania, zirconia, alumina, and the like.

Particularly preferred are the functionalized styrene-divinylbenzene copolymers, exemplified in the Examples by the various Amberlyst®-brand resins.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, 5, 6, from 1 to 9, from 3.6 to 4.6, from 3.5 to 9.9, and so forth.

All references to singular characteristics or limitations of the present invention shall include the corresponding plural characteristic or limitation, and vice-versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods of the present invention can comprise, consist of, or consist essentially of the essential elements and limitations of the method described herein, as well as any additional or optional ingredients, components, or limitations described herein or otherwise useful in synthetic organic chemistry.

DETAILED DESCRIPTION

Described herein is a method to make the commercially important compounds sorbic acid (5) and 1,3-pentadiene (6) via a ring-opening reaction of parasorbic acid (4):

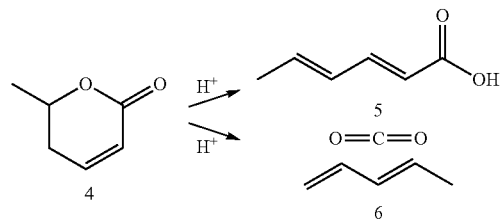

The process may also optionally start further upstream, starting with 4-hydroxy-6-methyl-2-pyrone (HMP, 1), to include a branching point that can be utilized to fabricate 3-penten-2-one (7) (with carbon dioxide being formed as a byproduct):

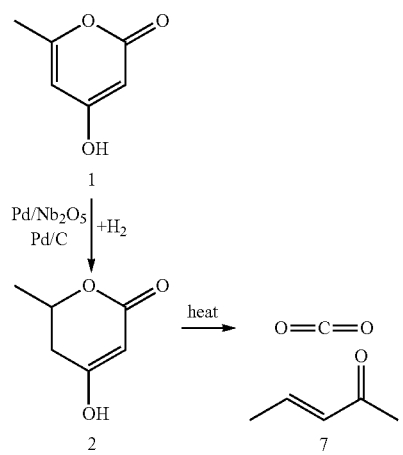

Of particular note is that the parasorbic acid reactant 4 may be obtained a renewable feed stock chemical 4-hydroxy-6-methyl-2-pyrone (HMP, 1). Thus, the crux of the present method is shown in Reaction Scheme 1 (which is also reproduced in the Examples). The numbering scheme for the various compounds is used consistently through the specification:

Reaction Scheme 1

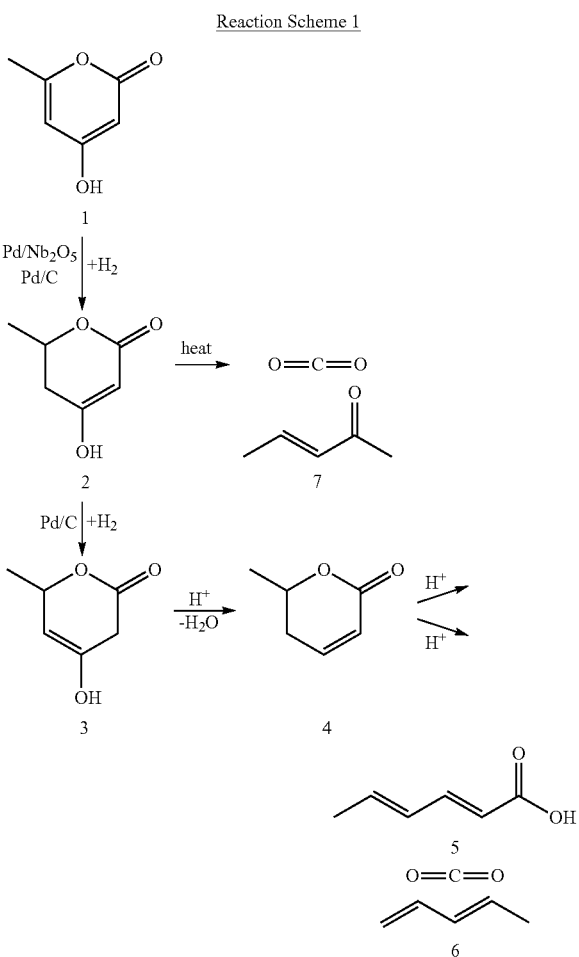

Five of the six reactions described in Reaction Scheme 1 are catalyzed by heterogeneous catalysts, preferably solid acid catalysts. The sixth reaction, the conversion of 5,6-dihydro-4-hydroxy-6-methyl-2H-pyrone (2) to 3-penten-2-one (7) takes place by thermal ring-opening of 2.

As depicted in Reaction Scheme 1, the preferred precursor to begin the process is 4-hydroxy-6-methyl-2-pyrone (HMP, 1). HMP is conventionally produced from acetic acid. However, it can be produced from sugars such as glucose using recombinant bacteria or yeast. See Xie D. M. et al. *Biotech. Bioeng.* 2006, 93, 727; Zha W. et al. *JACS* 2004, 126, 4534; and Richardson M. T. et al. *Metab. Eng.* 1999, 1, 180. This is important both economically and ecologically because the HMP precursor used in the present method can be fabricated de novo from renewable resources. Thus, the present method constitutes a bio-renewable platform from which a host of value-added chemicals can be derived. All of sorbic acid (5), 1,3-pentadiene (6), and 3-penten-2-one (7) can be made from HMP (1) using the methods described herein. Conventionally, all three of these compounds are obtained from nonrenewable petroleum-based feedstocks.

Overall, six distinct reactions may optionally be used in the method:
 (a) Partial hydrogenation of HMP (1) to DHHMP (2)
 (b) Complete hydrogenation of HMP (1) to 4-HMTHP (3).
 (c) Thermal decomposition of DHHMP (2) to PO (7).
 (d) Dehydration of 4-HMTHP (3) to PSA (4).
 (e) Ring-opening of PSA (4) to SA (5).
 (f) Decarboxylation of PSA (4) to PD (6).

The partial hydrogenation of HMP (1) to DHHMP (2) has been described in the literature, and can be accomplished either stereoselectively using Pd-based catalysts with chiral modifiers (Huck et al. (2003) *J. Catal.* 219:41), or non-stereoselectively using Pd- or Ni-based catalysts in alcohol solvents (Barcardit et al. (1980) *Tetrahedron Lett.* 21: 551). In the present method, stereoselectivity is not critical, so Pd- or Ni-based catalysts are preferred. As shown in the Examples, a Pd—$Nb_2O_5$ catalyst in butanol was used with great success. Overall yields were as high as 92%. The partial hydrogenation reaction is preferably carried out at a temperature from about 300 to 400 K (26.8° C. to 126.8° C.), and a $H_2$ partial pressure from about 25 psi to 200 psi. Lower alcohols are the preferred solvent, e.g., ethanol, propanol, butanol, etc., although carboxylic acids such as acetic acid may also be used as a solvent. As shown in Table 1, using 1-butanol as the solvent, 100 psi PH2, and carrying out the reaction at 343 K for five (5) hours, the yield of DHHMP (2) was 92%.

The complete hydrogenation of HMP (1) to 4-HMTHP (3) is preferably accomplished in a single step using a Pd-based catalyst dispersed on a support, preferably Pd/C, using an alcohol or THF as the solvent. (This is distinct from Barcardit et al. (1980) *Tetrahedron Lett.* 21: 551, in which this same complete hydrogenation is accomplished in two steps—a first partial hydrogenation to DHHMP (2), followed by a second hydrogenation to 4-HMTHP (3).) As shown in Table 2, the single-step complete hydrogenation described herein is very close to quantitative. With reactions times of from about 6 to about 12 hours, at 323 K, and 300 psi $P_{H2}$, yields of 4-HMTHP (3) were greater than 99%. Again, lower alcohols are the preferred solvent (ethanol, propanol, butanol, etc.), as well as THF.

If 3-penten-2-one (PO, 7) is a desired product, DHHMP (2) can be thermally decomposed to PO (7). There is no known literature precedent for this reaction. The conversion is quantitative. Preferred temperatures for the thermal degradation are from about 343.15 K to about 543.15 K (about 70° C. to about 270° C.), at pressures ranging from about 100 psi to about 600 psi. The DHHMP is preferably in an aqueous solution of from about 1 wt % to the solubility limit of DHHMP in water. At 2 wt % DHHMP in water, and 453 K and 493 K, there was complete conversion of DHHMP to PO. PO and carbon dioxide were the only products detected. See Example 3.

To use the method to make sorbic acid (5) and/or pentadiene (6), 4-HMTHP (3) is dehydrated to yield to PSA (4). The PSA (4) can then be ring-opened to yield sorbic acid (5) or decarboxylated to yield pentadiene (6). The preferred means to accomplish the dehydration is to use a solid acid catalyst. As noted above, any solid acid catalyst now know or developed in the future can be used. See Example 4 for specifics. THF is the preferred solvent, although any suitable aprotic solvent may be used (other linear or cyclic ethers, dimethyl sulfoxide, dimethylformamide, dioxane, etc.). The reaction is preferably carried out at a temperature from about 300 K to about 500 K, more preferably from about 353.15 K to about 413.15 K (about 80° C. to about 140° C.). The reaction is also preferably carried out at increased pressure, about 100 to 500 psi of an inert gas —$N_2$, He, Ar, etc. As shown in Example 4, under these conditions, the dehydration reaction is quantitative.

With parasorbic acid (4) in hand, the ring can either be opened to yield sorbic acid (5) or the ring can be decarboxylated to yield pentadiene (6).

There are two very old literature precedents for ring-opening PSA (4) to yield sorbic acid (5). See Fownes G. (1872), "A Manual of Elementary Chemistry, 11$^{th}$ Ed.," Henry C. Lea, Philadelphia, Pa.; and Roscoe H. E. (1890), "A Treatise on Chemistry, Vol. III," Macmillan & Co., New York, N.Y. In both literature precedents, the PSA was heated in the presence of KOH or HCl to yield sorbic acid. In the present method, the PSA ring is opened in the presence of a solid-acid catalyst, under an inert atmosphere (He, Ar, $N_2$, etc.). Polar, aprotic solvents are preferred. However, as noted in the Examples, a mixed solvent of THF and a small amount of water may also be used. See Table 5 for exemplary reaction conditions. As for the earlier steps that use a solid acid catalysts, any solid acid catalyst now known or developed in the future may be used in the ring-opening reaction. The Amberlyst®-brand catalysts described in the Examples are preferred. The reaction is preferably carried out at a temperature from about 300 K to about 425 K, more preferably from about 353.15 K to about 413.15 K (about 80° C. to about 140° C.), and at a pressure of about 100 to 500 psi of the inert gas. The reaction is not stereoselective, although the E, E conformation predominates in the product SA formed. Sorbic acid is the only major product detected. The best total yield obtained in the Examples for the entire process from HMP (1) to sorbic acid (5) was 64%. Selectivity for the ring-opening reaction of parasorbic acid to sorbic acid was greater than 80%.

The parasorbic acid (4) may also be decarboxylated to yield pentadiene (i.e., piperylene, 6). This reaction is also catalyzed using a solid acid catalyst, but under more rigorous conditions than the ring-opening dehydration described in the immediately preceding paragraph. For decarboxylation, a higher temperature range is preferred, from about 400 to about 600 K. As shown in the Examples, good conversion from 4 to 6 was accomplished at a reaction temperature of 443 K. Again, the reaction is carried out over a solid acid catalyst, under a pressurized inert atmosphere (100 to 500 psi of the inert gas). Protic polar and aprotic polar solvents are preferred. In the Examples, the decarboxylation reaction was carried out in a 1:1 mixture of water and THF.

EXAMPLES

The following Examples are included solely to provide a more detailed description of the invention disclosed and claimed herein. The Examples do not limit the scope of the claims in any fashion.

General Methods:

Quantification was performed using a gas chromatograph (Shimadzu GC-2010; Shimadzu Scientific Instruments, Columbia, Md.) equipped with a flame-ionization detector (FID). Identification of products in the liquid phase was performed using a gas chromatograph-mass spectrometer (Shimadzu Corp., GCMS-QP2010S) equipped with a Rxi®-brand SHRXI-5MS capillary column (30 m×0.25 mm×0.25 μm) (Restek Corporation, Bellefonte, Pa.). Gas phase products were collected in a gas bag and analyzed using a Carle gas chromatograph (Series 400 AGC; Carle Instruments, Inc. Gaithersburg, Md., now defunct) equipped with a thermal conductivity detector (TCD) and a Porapak® Q-brand packed column (Alltech Associates, Inc., Deerfield, Ill.), and a Varian gas chromatograph (Saturn 3; Varian, Inc., a wholly-owned subsidiary of Agilent Technologies, Inc., Santa Clara, Calif.) equipped with a FID and a GS-Q column (J&W Scientific, also a wholly-owned subsidiary of Agilent).

General Synthetic Approach:

The reactions described in the Examples that follow are summarized in Reaction Scheme 1:

Reaction Scheme 1: Key: 4-hydroxy-6-methyl-2-pyrone (HMP, 1); 5,6-dihydro-4-hydroxy-6-methyl-2H-pyran-2-one (DHHMP, 2); 4-hydroxy-6-methyltetrahydro-2-pyrone (4-HMTHP, 3); 6-methyl-5,6-dihydro-2-pyrone/parasorbic acid (PSA, 4); 2,4-hexadienoic acid/sorbic acid (SA, 5); 1,3-pentadiene/piperylene (PD, 6); 3-penten-2-one (PO, 7).

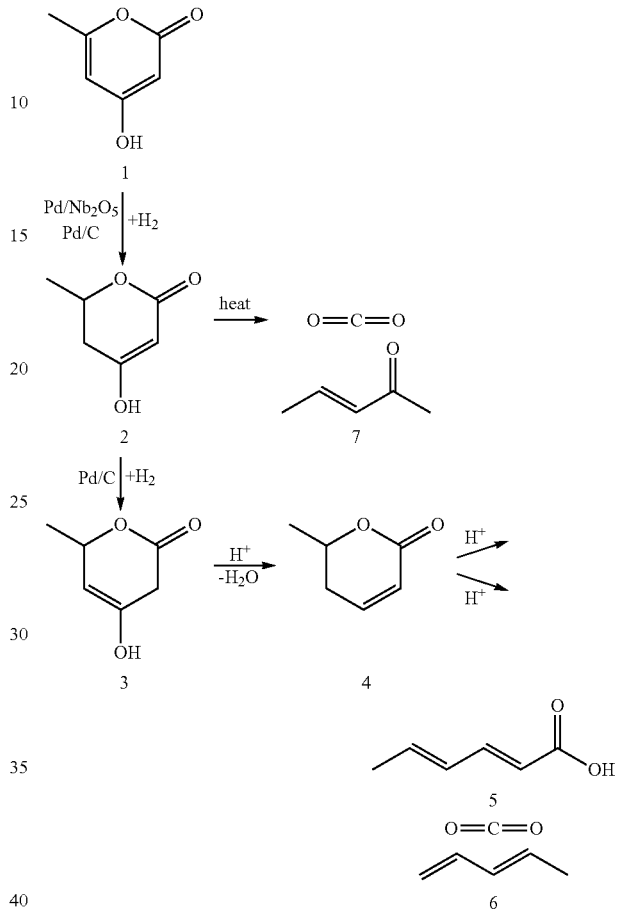

Example 1

Partial Hydrogenation of 4-Hydroxy-6-methyl-2-pyrone (HMP, 1) to 5,6-Dihydro-4-hydroxy-6-methyl-2H-pyran-2-one (DHHMP, 2)

Catalyst Preparation: 5 wt % Pd/$Nb_2O_5$ was prepared by the incipient wetness impregnation method, using an aqueous solution of Pd(II)$NO_3$ as the precursor. The catalysts were dried at 393 K for 1 h, calcined at 573 K for 5 h in 60 cc (STP)/min flowing air, and then reduced at 623 K for 5 h in 60 cc (STP)/min flowing $H_2$. Finally, the catalyst was passivated with 60 cc (STP)/min flowing 2% $O_2$ in He for 2 h at room temperature.

Experimental: The reactions were performed in a 50 mL batch reactor (Parr Instruments, Moline, Ill.). 5 wt % Pd/$Nb_2O_5$ was used as the catalyst, with 1.8 wt % HMP as the reactant in all cases. The mass ratio of catalyst to HMP was 1:1.7 in all cases. It was found that increased temperature yielded increased product degradation. It was also found that higher $H_2$ pressures caused further hydrogenation of DHHMP to 4-HMTHP and subsequently to δ-hexalactone (HL). Additionally, the solvent has an effect on product selectivity. The highest selectivity to DHHMP (92%, see Table 1) was attained when 1-butanol was employed as the solvent. The complete hydrogenation reaction from HMP (1) to 4-HMTHP (3) is depicted in Reaction Scheme 2. Table 1 presents the results for the partial hydrogenation reaction of HMP (1) to DHHMP (2) over 5 wt % Pd/Nb$_2$O$_5$ at various temperatures, hydrogen partial pressures, and using different solvents.

Reaction Scheme 2: Complete hydrogenation of HMP to 4-HMTHP over 10 wt % Pd/C.
Key: 4-hydroxy-6-methyl-2-pyrone (HMP, 1); 5,6-dihydro-4-hydroxy-6-methyl-2H-pyran-2-one (DHHMP, 2); 4-hydroxy-6-methyltetrahydro-2-pyrone (4-HMTHP, 3); δ-hexalactone (HL, 8).

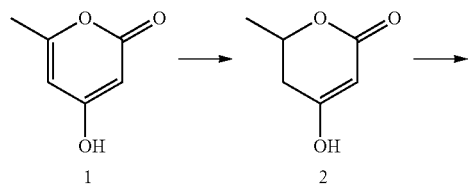

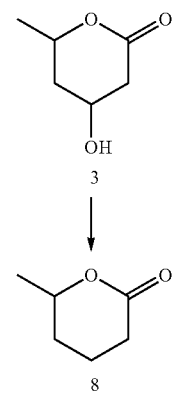

TABLE 1

Partial Hydrogenation of 4-Hydroxy-6-methyl-2-pyrone (HMP) to 5,6-Dihydro-4-hydroxy-6-methyl-2H-pyran-2-one (DHHMP) over 5 wt % Pd/Nb$_2$O$_5$.

| Solvent | Time (h) | P$_{H2}$ (psi) | T (K) | Yield of DHHMP (%) | Yield of HL (%) | Carbon balance (%) |
|---|---|---|---|---|---|---|
| 2-Propanol | 5 | 100 | 323 | 79 | 21 | >99.9 |
| 2-Propanol | 5 | 100 | 343 | 15 | 59 | 74 |
| 2-Propanol | 5 | 100 | 363 | 23 | 29 | 52 |
| 2-Propanol | 5 | 50 | 343 | 46 | 26 | 72 |
| Acetic acid | 5 | 100 | 343 | 48 | 20 | 68 |
| Ethanol | 5 | 100 | 343 | 60 | 7 | 67 |
| 1-Butanol | 5 | 100 | 343 | 92 | 1 | 93 |

Example 2

Complete Hydrogenation of 4-Hydroxy-6-methyl-2-pyrone (HMP, 1) to 5,6-Dihydro-4-hydroxy-6-methyl-2H-pyran-2-one (4-HMTHP, 3)

Catalyst preparation: 10 wt % Pd/C (Sigma-Aldrich, Milwaukee, Wis.) was reduced at 533 K for 4 h in 60 cc (STP)/min flowing H$_2$, and then passivated with 60 cc (STP)/min flowing 2% O$_2$ in He for 2 h at room temperature.

Experimental: The reactions were performed in a 50 mL batch reactor (Parr Instruments). 10 wt % Pd/C was used as the catalyst, with 1.8 wt % HMP as the reactant in all cases. Near-quantitative yield of 4-HMTHP was achieved in all cases, with δ-hexalactone (HL) being the only by-product detected. See Table 2.

TABLE 2

Complete Hydrogenation of 4-Hydroxy-6-methyl-2-pyrone (HMP, 1) to 5,6-Dihydro-4-hydroxy-6-methyl-2H-pyran-2-one (4-HMTHP, 3) over 10 wt % Pd/C, 323 K.

| Solvent | Catalyst:HMP (g:g) | Time (h) | P$_{H2}$ (psi) | HMP Conversion (%) | Selectivity to DHHMP (%) | Selectivity to 4-HMTHP (%) | Selectivity to HL (%) |
|---|---|---|---|---|---|---|---|
| 1-Butanol | 1:1 | 8 | 300 | 98 | 0 | 99.4 | 0.6 |
| THF | 1:1 | 6 | 300 | >99 | 0 | >99 | Not detected |
| THF | 1:1 | 8 | 300 | >99 | 0 | >99 | Not detected |
| THF | 1:1 | 12 | 300 | >99 | 0 | >99 | Not detected |
| THF | 1:2 | 8 | 500 | >99 | 35.2 | 64.5 | 0.3 |
| THF | 1:2 | 12 | 500 | >99 | 0 | 96.2 | 3.8 |

Example 3

Thermal Decomposition of 5,6-Dihydro-4-hydroxy-6-methyl-2H-pyran-2-one (DHHMP, 2) to 3-Penten-2-one (PO, 7)

Experimental: The decarboxylation of DHHMP (2) to PO (7) was performed in a pressurized (500 psi) upflow reactor, using 2 wt % DHHMP in water as the feed (0.04 mL/min) and He as the carrier gas (14 cc (STP)/min). Decomposition of DHHMP in water was noted to occur across a temperature range of 343-543 K. The molar ratio of $CO_2$ to converted DHHMP was close to 1:1 in all runs. In addition to $CO_2$, PO was the only other product observed. Due to low reactant and product concentrations, and reactant feed rate, the overall carbon balance did not close completely. At 100% conversion of DHHMP, 60% molar yield to PO was noted. Complete results are presented in Table 3.

TABLE 3

Thermal Decomposition of 5,6-Dihydro-4-hydroxy-6-methyl-2H-pyran-2-one (DHHMP, 2) to 3-Penten-2-one (PO, 7).

| T (K) | Yield of PO (%) | Carbon balance (%) | $CO_2$:DHHMP converted (mol:mol) |
|---|---|---|---|
| 493 | 50.1 | 57.6 | 0.95:1 |
| 453 | 59.7 | 66.3 | 0.99:1 |

Reaction conditions: 2 wt % DHHMP in $H_2O$ (0.04 mL/min), 500 psi, 14 cc (STP)/min He. Complete conversion of DHHMP in all cases.

Example 4

Dehydration of 4-hydroxy-6-methyltetrahydro-2-pyrone (4-HMTHP, 3) to Parasorbic acid (PSA, 4)

Catalyst preparation: Amberlyst®-15 and Amberlyst®-70 resins (Rohm & Haas, a wholly owned subsidiary of Dow Chemical Co., Midland, Mich.) were washed with deionized water, dried at 393 K for 16 h, and mechanically crushed to a fine powder. The powder was then sifted through a sieve (Tyler mesh size 42, standard US mesh size 45) to remove large particulates.

Experimental: The dehydration of 4-HMTHP was performed over solid acid catalysts, such as Amberlyst®-15 and Amberlyst®-70 resins. Dehydrations were performed in a 50 mL batch reactor (Parr Instruments) under inert atmosphere (300 psi He), 80-140° C., 8-12 h, using 1.8 wt % 4-HMTHP in THF as the reactant solution. Selectivities to PSA was >99% in all cases. See Table 4 for complete results.

TABLE 4

Reaction Conditions Examined for the Dehydration of 4-Hydroxy-6-methyltetrahydro-2-pyrone (4-HMTHP, 3) to Parasorbic acid (PSA, 4) (THF as solvent, 300 psi He).

| Catalyst | Catalyst:4-HMTHP (g:g) | Time (h) | T (K) | Conversion (%) |
|---|---|---|---|---|
| Amberlyst ®-15 | 1:0.8 | 8 | 353 | 99 |
| Amberlyst ®-15 | 1:0.8 | 8 | 373 | 99 |
| Amberlyst ®-15 | 1:0.8 | 12 | 393 | 99 |
| Amberlyst ®-70 | 1:0.8 | 12 | 413 | 99 |
| Amberlyst ®-70 | 1:0.7 | 12 | 373 | 99 |
| Amberlyst ®-70 | 1:0.7 | 8 | 373 | 80 |
| Amberlyst ®-70 | 1:0.7 | 4 | 373 | 60 |

Complete conversion of 4-HMTHP, and no by-products detected in all runs.

Example 5

Combined Dehydration and Ring-Opening of 4-Hydroxy-6-methyltetrahydro-2-pyrone (4-HMTHP, 3) to Sorbic Acid (SA, 5)

Catalyst preparation: Amberlyst®-70 resin was washed with deionized water, dried at 393 K for 16 h, and mechanically crushed to a fine powder. The powder was then sifted through a sieve (Tyler mesh size 42, standard US mesh size 45) to remove large particulates.

Experimental: The combined dehydration of 4-HMTHP and subsequent ring-opening of PSA was performed over the solid acid catalyst, Amberlyst®-70. Reactions were performed in a 50 mL batch reactor (Parr Instruments) under inert atmosphere (300 psi He), using 1.8 wt % 4-HMTHP in THF as the reactant solution. In some cases, a small amount of deionized water was added to achieve a final solvent composition of $H_2O$:THF=0.04:1 (g:g). (See Table 5, entries 5-7.) The presence of water retarded the rate of ring-opening. The reaction temperature was controlled such that two different stages were employed: $t_1$ (h) and $T_1$ (K), and $t_2$ (h) and $T_2$ (K). In other words, the reaction temperature was held at $T_1$ for a duration of $t_1$, and then at $T_2$ for $t_2$. Note that $T_1$=373 K for all experiments. It was found that a lower reaction temperature ($T_2$) resulted in higher selectivities to SA formed with respect to the amount of PSA converted. Gas chromatography-mass spectrometry (GC-MS) analysis of the product mixture indicated that in addition to E, E-sorbic acid (SA) being formed as the major product, a small amount of other SA isomers was also present. The amount of other SA isomers was minor (1-5% yield with respect to 4-HMTHP). The maximum yield of SA formed with respect to HMP was 64%.

See Reaction Scheme 3, which depicts the dehydration of 4-hydroxy-6-methyltetrahydro-2-pyrone (4-HMTHP, 3) and ring-opening of parasorbic acid (PSA, 4) over Amberlyst®-70 resin. Complete results are presented in Table 5.

Reaction Scheme 3: Dehydration of 4-hydroxy-6-methyltetrahydro-2-pyrone (4-HMTHP, 3) and ring-opening of parasorbic acid (PSA, 4) over Amberlyst®-70 resin. Key: 4-hydroxy-6-methyltetrahydro-2-pyrone (4-HMTHP, 3); 6-methyl-5,6-dihydro-2-pyrone/parasorbic acid (PSA, 4); 2,4-hexadienoic acid/sorbic acid (SA, 5); 1,3-pentadiene/piperylene (PD, 6).

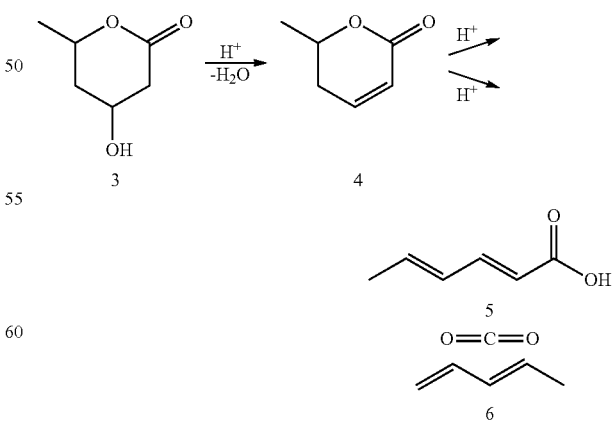

TABLE 5

Dehydration of 4-Hydroxy-6-methyltetrahydro-2-pyrone (4-HMTHP, 3) and Ring-Opening of Parasorbic Acid (PSA, 4) over Amberlyst ®-70 Resin.

| Entry | $t_1$ (h) | $t_2$ (h) | $T_2$ (K) | PSA yield wrt 4-HMTHP (%) | E,E-SA yield wrt 4-HMTHP (%) | SA (total) yield wrt 4-HMTHP (%) | $PD^i$ yield wrt 4-HMTHP (%) | Selectivity to SA (total) wrt PSA converted[ii] (%) | Carbon balance (%) | SA (total) yield wrt HMP (%) |
|---|---|---|---|---|---|---|---|---|---|---|
| 1 | 12 | 12 | 443 | 19.5 | 61.0 | 65.8 | 0.9 | 81.8 | 86.2 | 63.2 |
| 2 | 0 | 12 | 443 | 7.8 | 61.9 | 66.7 | 1.1 | 72.4 | 75.6 | 64.1 |
| 3 | 12 | 18 | 443 | 8.9 | 61.4 | 66.1 | 1.5 | 72.5 | 76.5 | 63.4 |
| 4 | 12 | 12 | 453 | 3.3 | 59.6 | 65.4 | 1.7 | 67.7 | 70.4 | 62.8 |
| 5[iii] | 12 | 12 | 443 | 51.9 | 45.8 | 46.4 | 0.9 | 96.6 | 99.2 | 44.5 |
| 6[iii] | 0 | 24 | 443 | 20.3 | 60.9 | 61.8 | 2.0 | 84.0 | 84.1 | 59.3 |
| 7[iii] | 0 | 24 | 433 | 45.9 | 50.5 | 51.4 | 0.8 | 95.1 | 98.1 | 49.4 |

Reaction conditions were 300 psi He, catalyst: 4-HMTHP = 1:1.4 (g:g), THF as solvent; complete conversion of 4-HMTHP in all runs.
The reaction temperature profile consisted of two steps: $t_1$ (h) and $T_1$ (K), and $t_2$ (h) and $T_2$ (K). $T_1$ = 373 K in all experiments.
[i]Estimated based on amount of $CO_2$ detected in gas phase;
[ii]assuming quantitative yield of PSA from 4-HMTHP;
[iii]$H_2O$:THF ~0.04:1.

Example 6

Decarboxylation of Parasorbic Acid (PSA, 4) to 1,3-Pentadiene (PD, 6)

Catalyst preparation: Amberlyst®-70 resin (Rohm & Haas) was washed with deionized water, dried at 393 K for 16 h, and mechanically crushed to a fine powder. The powder was then sifted through a sieve (Tyler mesh size 42, standard US size 45) to remove large particulates.

Experimental: The decarboxylation of PSA to PD was performed over Amberlyst®-70-brand solid acid catalyst. Experiments were performed in a 50 mL batch reactor (Parr Instruments) under inert atmosphere (300 psi He), using 0.9 wt % 4-HMTHP in a THF-$H_2O$ mixture (THF:$H_2O$=1:1 (g:g)) as the reactant solution. After reaction, the gas phase was sampled and analyzed using GC, and 1,3-pentadiene and $CO_2$ were detected. Analysis of the liquid phase showed that 12% conversion of PSA was attained, and traces of 1,3-pentadiene were detected. An approximate quantitative analysis of the gas phase indicated that the molar ratio of $CO_2$ produced to PSA converted was 1.1:1. Complete results are presented in Table 6.

TABLE 6

Decarboxylation of Parasorbic acid (PSA, 4) to 1,3-Pentadiene (PD, 6) over Amberlyst ®-70-brand Resin.

| Time (h) | T (K) | Catalyst:PSA (g:g) | PSA conversion (%) | $CO_2$:PSA converted (mol:mol) |
|---|---|---|---|---|
| 12 | 443 | 1:0.7 | 11.5 | 1.1:1 |

Reaction conditions: 0.9 wt % PSA in THF-$H_2O$ mixture (THF:$H_2O$ = 1:1 (g:g)), 443 K, 300 psi He, 12 h.

What is claimed is:

1. A method of making sorbic acid and pentadiene, the method comprising:
   (a) converting 4-hydroxy-6-methyl-2-pyrone (HMP) to parasorbic acid (PSA); and then
   (b) ring-opening the PSA from step (b) by contacting the PSA with a solid acid catalyst to yield sorbic acid or pentadiene.

2. The method of claim 1, wherein step (a) comprises hydrogenating the HMP in the presence of a catalyst comprising one or more noble metals.

3. The method of claim 1, wherein step (a) comprises hydrogenating the HMP in the presence of a catalyst comprising palladium.

4. The method of claim 3, wherein step (a) comprises hydrogenating the HMP in the presence of a catalyst comprising palladium and niobium.

5. The method of claim 1, wherein step (a) comprises hydrogenating the HMP in a solvent selected from the group consisting of $C_1$- to $C_6$-alcohols and $C_1$- to $C_6$-carboxylic acids.

6. The method of claim 1, wherein step (a) comprises
   (a)(i) hydrogenating 4-hydroxy-6-methyl-2-pyrone (HMP) to yield 5,6-dihydro-4-hydroxy-6-methyl-2H-pyran-2-one (4-HMTHP); and then
   (a)(ii) dehydrating the 4-HMTHP from step (a)(i) by contacting the 4-HMTHP with a solid acid catalyst to yield parasorbic acid (PSA).

7. The method of claim 6, wherein solid acid catalysts used in steps
   (a)(ii) and (b) are independently selected from the group consisting of functionalized styrene-divinylbenzene copolymers and functionalized tetrafluoroethylene-fluoropolymer copolymers.

8. The method of claim 1, wherein step (b) is carried out in a polar, aprotic solvent, or a mixed solvent comprising water and a polar, aprotic solvent.

9. The method of claim 8, wherein step (b) is carried out in a mixed solvent comprising tetrahydrofuran and water.

10. A method of making sorbic acid and pentadiene, the method comprising:
    (a) hydrogenating 4-hydroxy-6-methyl-2-pyrone (HMP) to yield 4-hydroxy-6-methyltetrahydro-2-pyrone (4-HMTHP); and then
    (b) dehydrating the 4-HMTHP from step (a) by contacting the 4-HMTHP with a solid acid catalyst to yield parasorbic acid (PSA); and then
    (c) ring-opening the PSA from step (b) by contacting the PSA with a solid acid catalyst to yield sorbic acid or pentadiene.

11. The method of claim 10, wherein step (a) comprises hydrogenating the HMP in the presence of a catalyst comprising one or more noble metals.

12. The method of claim 10, wherein step (a) comprises hydrogenating the HMP in the presence of a catalyst comprising palladium.

13. The method of claim 12, wherein step (a) comprises hydrogenating the HMP in the presence of a catalyst comprising palladium and niobium.

14. The method of claim 10, wherein step (a) comprises hydrogenating the HMP in a solvent selected from the group consisting of $C_1$- to $C_6$-alcohols and $C_1$- to $C_6$-carboxylic acids.

15. The method of claim 10, wherein solid acid catalysts used in steps (b) and (c) are independently selected from the group consisting of functionalized styrene-divinylbenzene copolymers and functionalized tetrafluoroethylene-fluoropolymer copolymers.

16. The method of claim 10, wherein step (c) is carried out in a polar, aprotic solvent, or a mixed solvent comprising water and a polar, aprotic solvent.

17. The method of claim 16, wherein step (c) is carried out in a mixed solvent comprising tetrahydrofuran and water.

18. A method of making sorbic acid, pentadiene, or 3-penten-2-one, the method comprising:
  (a) partially hydrogenating 4-hydroxy-6-methyl-2-pyrone (HMP) to yield 5,6-dihydro-4-hydroxy-6-methyl-2H-pyran-2-one (4-DHMMP); then
  (b) if 3-penten-2-one is desired, thermally decomposing the 4-DHMMP to yield 3-penten-2-one;
  (c) if sorbic acid or pentadiene are desired, hydrogenating the 4-DHMMP of step (a) to yield 4-hydroxy-6-methyltetrahydro-2-pyrone (4-HMTHP); then dehydrating the 4-HMTHP by contacting the 4-HMTHP with a solid acid catalyst to yield parasorbic acid (PSA); and then
  (d) ring-opening the PSA from step (c) by contacting the PSA with a solid acid catalyst to yield sorbic acid or pentadiene.

19. The method of claim 18, wherein steps (a) and (c) comprise performing the hydrogenation in the presence of a catalyst comprising one or more noble metals.

20. The method of claim 18, wherein steps (a) and (c) comprise performing the hydrogenation in the presence of a catalyst comprising palladium.

21. The method of claim 18, wherein step (a) comprises performing the partial hydrogenation in the presence of a catalyst comprising palladium and niobium.

22. The method of claim 18, wherein steps (a) and (c) comprises performing the hydrogenation in a solvent selected from the group consisting of $C_1$- to $C_6$-alcohols and $C_1$- to $C_6$-carboxylic acids.

23. The method of claim 18, wherein solid acid catalysts used in steps (c) and (d) are independently selected from the group consisting of functionalized styrene-divinylbenzene copolymers and functionalized tetrafluoroethylene-fluoropolymer copolymers.

24. The method of claim 18, wherein step (d) is carried out in a polar, aprotic solvent, or a mixed solvent comprising water and a polar, aprotic solvent.

25. The method of claim 24, wherein step (d) is carried out in a mixed solvent comprising tetrahydrofuran and water.

* * * * *